(12) United States Patent
Sekido et al.

(10) Patent No.: US 8,912,445 B2
(45) Date of Patent: Dec. 16, 2014

(54) CABLE ASSEMBLY

(75) Inventors: Takanori Sekido, Chofu (JP); Fukashi Yoshizawa, Ina (JP)

(73) Assignee: Olympus Corporation, Tokyo (JP)

( * ) Notice: Subject to any disclaimer, the term of this patent is extended or adjusted under 35 U.S.C. 154(b) by 382 days.

(21) Appl. No.: 13/345,804

(22) Filed: Jan. 9, 2012

(65) Prior Publication Data

US 2012/0103686 A1 May 3, 2012

Related U.S. Application Data

(63) Continuation of application No. PCT/JP2010/061207, filed on Jun. 30, 2010.

(30) Foreign Application Priority Data

Jul. 13, 2009 (JP) .................. 2009-164883

(51) Int. Cl.
 | | |
 |---|---|
 | H02G 15/02 | (2006.01) |
 | H02G 1/14 | (2006.01) |
 | A61B 1/00 | (2006.01) |
 | G02B 23/24 | (2006.01) |
 | H01R 13/02 | (2006.01) |

(52) U.S. Cl.
CPC .. H02G 1/14 (2013.01); A61B 1/00 (2013.01); G02B 23/2476 (2013.01); H01R 13/025 (2013.01)
USPC .......................... 174/74 R; 174/75 R; 174/78

(58) Field of Classification Search
CPC ............. H05K 1/00; H05K 3/00; H05K 9/00; H05K 13/00; H05K 2009/0007; H01R 3/00; H01R 4/00; H01R 4/10; H01B 1/00; H01B 5/00; H01B 7/08; H01B 7/04; H01B 7/02
USPC .......... 174/71 C, 72 R, 72 TR, 78, 36, 113 R, 174/117 R, 117 F, 117 FF, 84 R, 84 C, 75 C; 439/608, 610, 497
See application file for complete search history.

(56) References Cited

U.S. PATENT DOCUMENTS 3,878,341 A * 4/1975 Balde ........................... 307/113
4,606,598 A * 8/1986 Drzymkowski et al. . 439/607.12
(Continued)

FOREIGN PATENT DOCUMENTS

| | | |
|---|---|---|
| JP | 04-109511 | 4/1992 |
| JP | 4-179074 A | 6/1992 |

(Continued)

OTHER PUBLICATIONS

English Abstract of corresponding Japanese Patent Publication No. 09-090237, dated Apr. 4, 1997.

(Continued)

*Primary Examiner* — William H Mayo, III
(74) *Attorney, Agent, or Firm* — Scully, Scott, Murphy & Presser, P.C.

(57) ABSTRACT

A cable assembly includes: a plurality of cables; a cable fixing member that fixes the cables together; and conductor layers, wherein the cable assembly is formed with a connecting end surface that includes thereon connecting ends of the cables, and the conductor layers are provided to cover surfaces of the connecting ends that are on the connecting end surface.

6 Claims, 6 Drawing Sheets

(56) References Cited

U.S. PATENT DOCUMENTS

| | | | |
|---|---|---|---|
| 4,941,833 A * | 7/1990 | Noschese et al. | 439/92 |
| 5,042,971 A * | 8/1991 | Ambrose | 439/77 |
| 5,046,966 A * | 9/1991 | Snyder et al. | 439/579 |
| 5,281,762 A * | 1/1994 | Long et al. | 174/78 |
| 6,093,894 A * | 7/2000 | Carlson et al. | 174/117 F |
| 6,344,616 B1 * | 2/2002 | Yokokawa | 174/117 F |
| 6,380,485 B1 * | 4/2002 | Beaman et al. | 174/88 R |
| 6,585,528 B1 * | 7/2003 | Lin et al. | 439/76.1 |
| 6,606,787 B2 * | 8/2003 | Okumura et al. | 29/828 |
| 6,837,741 B2 * | 1/2005 | Kuwahara | 439/497 |
| 6,958,450 B2 | 10/2005 | Keser et al. | |
| 7,462,065 B1 * | 12/2008 | Zhao | 439/499 |
| 7,484,998 B2 * | 2/2009 | Benham | 439/579 |
| 7,628,647 B2 * | 12/2009 | Semba et al. | 439/579 |
| 7,973,239 B2 * | 7/2011 | Koyama et al. | 174/74 R |
| 2004/0190278 A1 | 9/2004 | Keser et al. | |

FOREIGN PATENT DOCUMENTS

| | | |
|---|---|---|
| JP | 07-029423 | 1/1995 |
| JP | 11-295617 A | 10/1999 |
| JP | 2000-277941 A | 10/2000 |
| JP | 2000-278837 A | 10/2000 |
| JP | 2001-014956 | 1/2001 |
| JP | 2003-178826 A | 6/2003 |
| JP | 2004-006113 | 1/2004 |
| JP | 2006-127790 | 5/2006 |
| JP | 3863583 | 10/2006 |
| JP | 2007-278810 A | 10/2007 |
| JP | 2007-335174 A | 12/2007 |
| WO | 2004/047509 A1 | 6/2004 |

OTHER PUBLICATIONS

International Search Report dated Oct. 5, 2010 issued in PCT/JP2010/061207.

Notice of Rejection dated Oct. 29, 2013 from related Japanese Application No. 2009-164883, together with an English language translation.

Extended Supplementary European Search Report dated May 8, 2014 from related European Application No. 10 79 9734.8.

* cited by examiner

US 8,912,445 B2

CABLE ASSEMBLY

CROSS-REFERENCE TO RELATED APPLICATIONS

This application is a continuation of PCT international application Ser. No. PCT/JP2010/061207 filed on Jun. 30, 2010 which designates the United States, incorporated herein by reference, and which claims the benefit of priority from Japanese Patent Application No. 2009-164883, filed on Jul. 13, 2009, incorporated herein by reference.

BACKGROUND OF THE INVENTION

1. Field of the Invention

The present invention relates to a cable assembly that can set a plurality of cables in contact as one bundle.

2. Description of the Related Art

Conventionally, a cable assembly is used in a distal-end circuit of an endoscope to set two or more cables in contact as one bundle. A small-sized cable assembly is implemented by shortening the length of a hard section that functions as a connecting terminal section. Cable assemblies have a plurality of cables, with the cables being fixed together by using an array block that forms a hard section, and they have a cable connecting end surface that is formed by polishing the distal ends of the fixed cables in such a manner that the distal ends together form the same plane. The cables are set in contact by using an anisotropic conductive adhesive film (ACF: Anisotropic Conductive Adhesive Film) or an anisotropic conductive adhesive paste (ACP: Anisotropic Conductive Adhesive Paste), which is applied to the cable connecting end surface. Thereby, the cables are set in contact as one bundle and the length of the hard section is set short.

SUMMARY OF THE INVENTION

A cable assembly according to an aspect of the present invention includes: a plurality of cables; a cable fixing member that fixes the cables together; and conductor layers, wherein the cable assembly is formed with a connecting end surface that includes thereon connecting ends of the cables, and the conductor layers are provided to cover surfaces of the connecting ends that are on the connecting end surface.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are described in detail below with reference to the accompanying drawings. It should be noted that the present invention is not limited to these exemplary embodiments.

Figure 1:
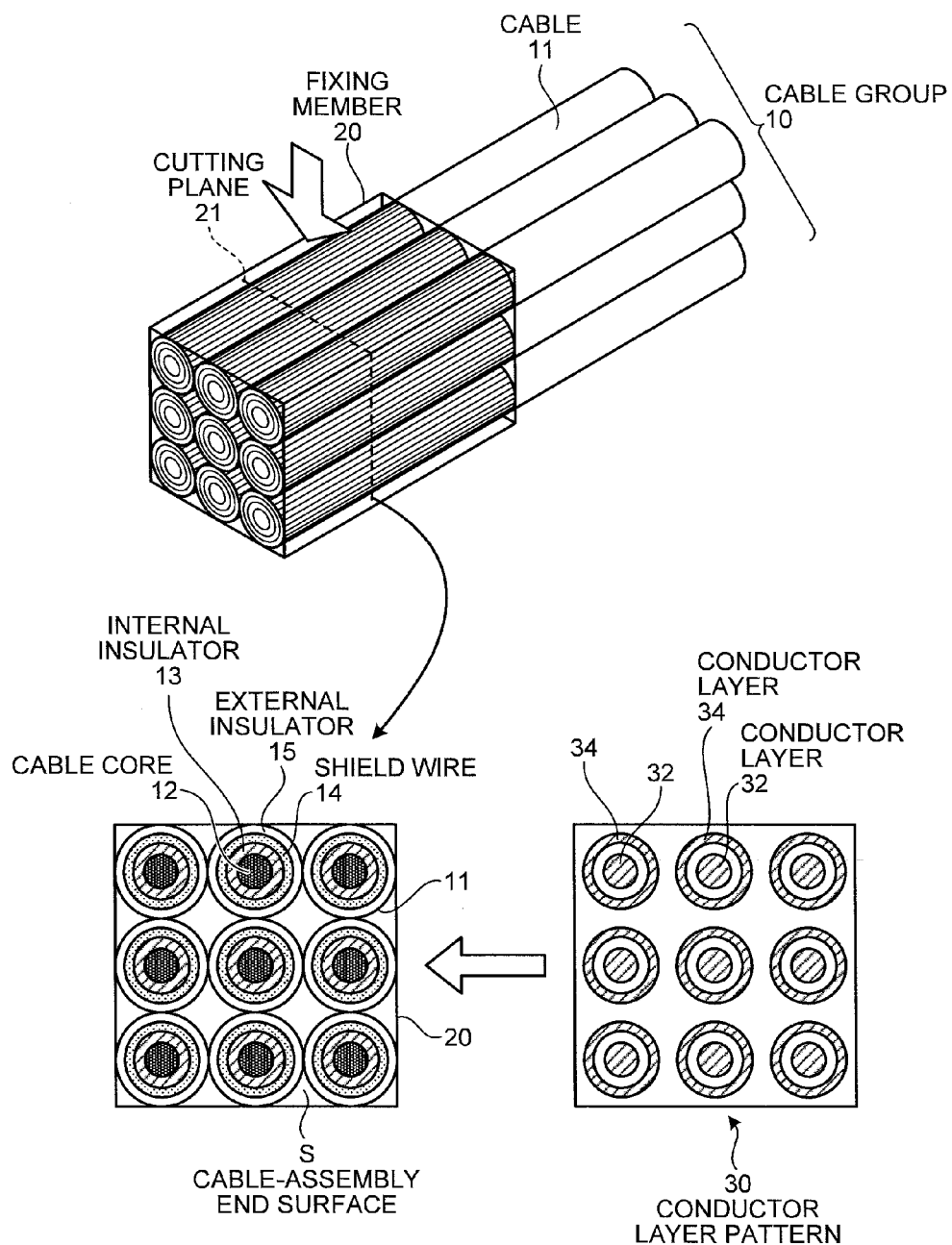
FIG. 1 is an explanatory diagram that explains production of a cable assembly according to an embodiment of the present invention.
Figure 2:
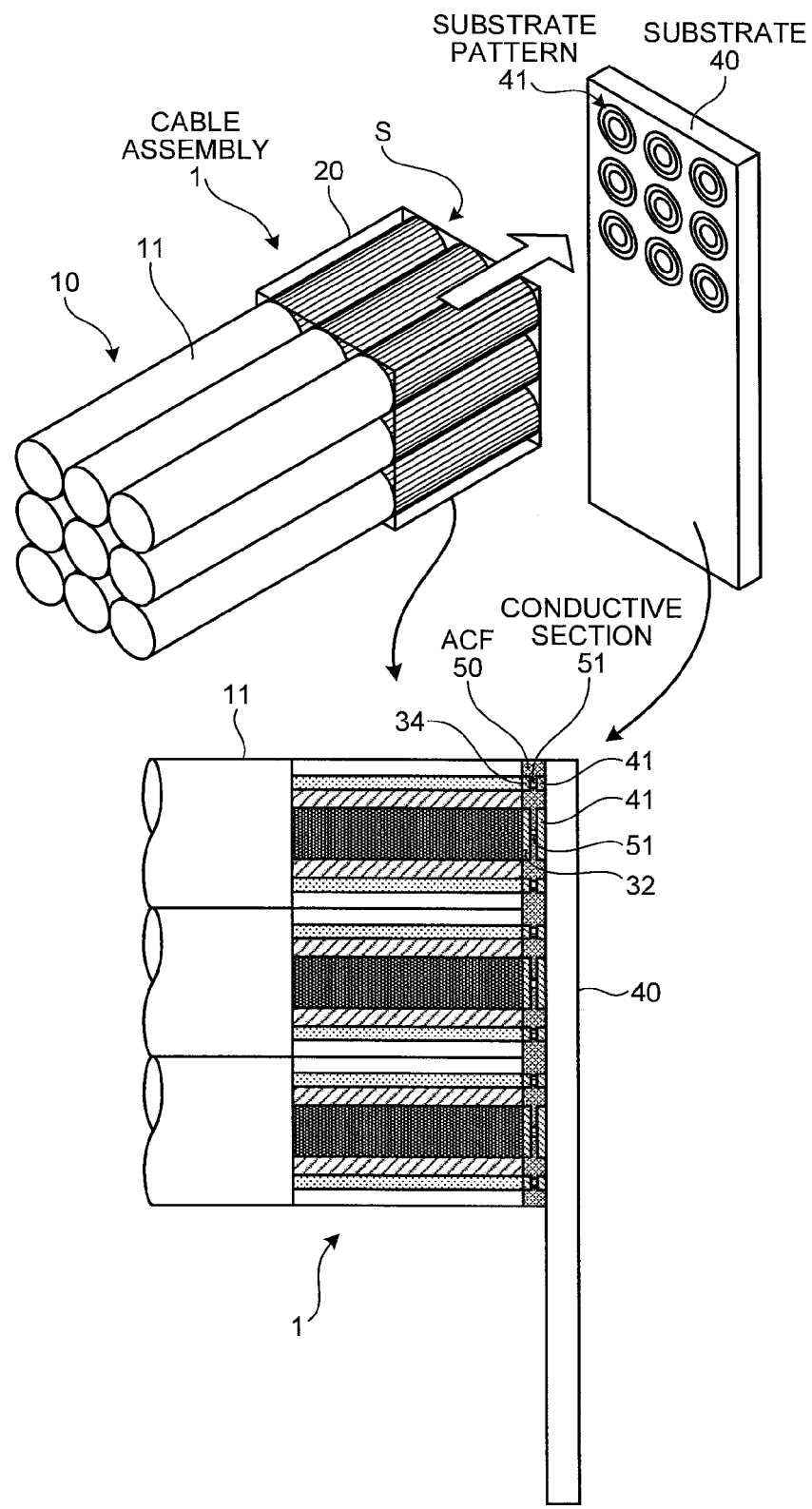
FIG. 2 is an explanatory diagram that explains a process of connecting the cable assembly to an external substrate.

FIG. 1 is an explanatory diagram that explains production of a cable assembly according to an embodiment of the present invention. FIG. 2 is an explanatory diagram that illustrates an application of the produced cable assembly. As illustrated in FIG. 1, in a cable assembly, a plurality of cables 11 are bound together, thereby forming a cable group 10, and the cables 11 of the cable group 10 are fixed to each other by using a fixing member 20 that is made of a resin, etc. In this fixed state, in order to form a cable-assembly end surface S that is a connecting end surface of the cable assembly, part of the fixing member 20 is cut along a cutting plane 21. In the cut surface, a connecting end surface, which leads to the cable group 10 is, is then polished so that the formed connecting end surface includes the connecting end of each of the cables 11 on the same plane.

Each of the cables 11 is a coaxial cable having the same diameter. A shield wire 14 is formed on an internal insulator 13, surrounding the outer circumference of a cable core 12. An external insulator 15 is formed on the outer circumference of the shield wire 14. Although, in FIG. 1, nine (3×3) cables 11 are adjacently arranged in parallel in such a manner that the cross section is substantially a rectangular, it is allowable to use an array block in which cable insertion holes are formed in advance. If so, the cables 11 are not adjacently arranged. It is preferable to perform cutting and polishing involving the array block.

When the cable-assembly end surface S is formed by the polishing process, corresponding conductor layers 32 and 34 in a conductor layer pattern 30 are formed on the connecting end surfaces, which are cross sections of the cable core 12 and the shield wire 14 of each cable 11. The conductor layers 32 and 34 are implemented by metallic films, and the conductor layer pattern 30 is formed by electrolytic plating, non-electrolytic plating, or spattering. The conductor layers 32 and 34 can have either a single-layer structure or a multilayer structure. A multilayer structure having a Ni/Au multilayer film, in which an Au layer is top layer and a Ni layer is under layer, is preferable because a strong bonding to a connecting end surface is formed. By using the Ni/Au multilayer film, various bonding methods become applicable, not only ACF and ACP bonding but also solder bump bonding and Au bump bonding, thereby increasing the flexibility in bonding.

A thus formed cable assembly 1 is connected, as illustrated in FIG. 2, to a substrate 40 on which a substrate pattern 41 is formed that corresponds to the conductor layer pattern 30 of the cable-assembly end surface S of the cable assembly 1. An anisotropic conductive resin material, such as an ACF 50, is inserted between the cable assembly 1 and the substrate 40. By thermal compression bonding using the anisotropic conductive resin material, a conductive section 51 is formed on a compressed area, and the cable assembly 1 and the substrate 40 are bonded together. Because the areas where the conductor layers 32 and 34 are formed are convex and are protruding outward from the cable-assembly end surface S, the areas are under a high pressure and thus the conductive section 51 is formed via a dense filler, etc., within the ACF 50.

Figure 3:
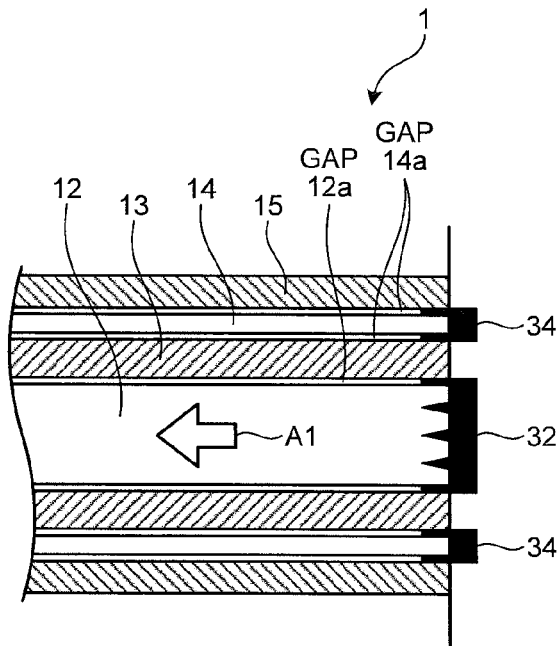
FIG. 3 is a cross-sectional view of a state of a conductor layer that is near the cable-assembly end surface.

In the present embodiment, the shapes of the conductor layers 32 and 34 are the same as the shapes of the cross sections of the cable core 12 and the shield wire 14, respectively. As illustrated in FIG. 3, the actual cables 11 have a gap 12a between the cable core 12 and the internal insulator 13 and a gap 14a between the shield wire 14 and either the internal insulator 13 or the external insulator 15. The conductor layers 32 and 34 are formed to be inserted in the gaps 12a and 14a, respectively, near the cable-assembly end surface S. In other words, the conductor layers 32 and 34 are formed to be inserted in the gaps 12a and 14a, respectively, like wedges. With a stress that occurs in a line-width direction near the cable-assembly end surface S, the cable core 12 and the internal insulator 13, the shield wire 14 and the internal insulator 13, and the shield wire 14 and the external insulator 15 are fixed together. In general, there is a concern that, due to a bending of the cables 11, which are not fixed together by the fixing member 20, or a change in temperature, etc., the cable core 12 and the shield wire 14 are pulled toward a direction indicated by an arrow A1; however, the above-mentioned fixing prevents the above problem, and connecting end surfaces are reliably formed on the cable-assembly end surface S. In other words, the conductor layers 32 and 34 function as stoppers that prevent the cable core 12 and the shield wire 14 from moving inwardly in the direction indicated by the arrow A1. If the cable core 12 and the shield wire 14 are formed by a plurality of wires, such as twisted wires, the conductor layers 32 and 34 are inserted between wires like wedges near the cable-assembly end surface S. A stress occurring in the line-width direction makes them function as stoppers.

Figure 4:
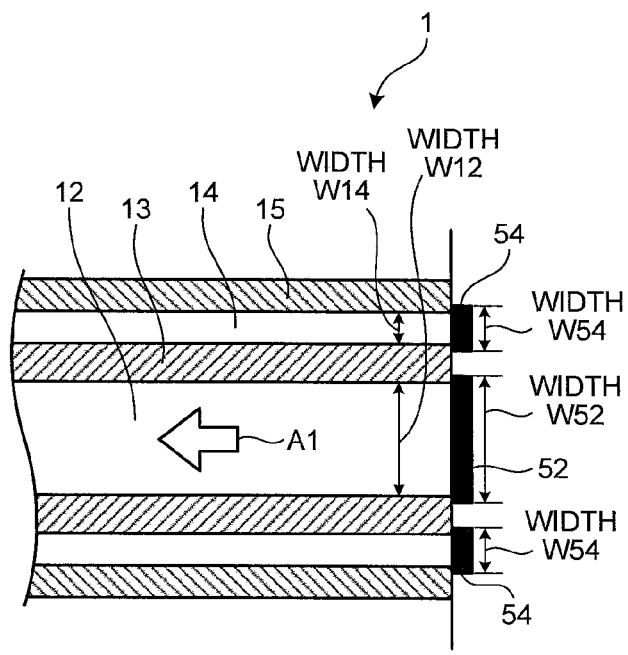
FIG. 4 is a cross-sectional view of a modification of the conductor layer.

As illustrated in FIG. 4, overlapping conductor layers 52 and 54 may be applied, the widths of which exceed the width W12 of the cable core 12 and the width W14 of the shield wire 14, respectively. That is, a width W52 of the conductor layer 52 satisfies W52>W12 and a width W54 of the conductor layer 54 satisfies W54>W14. In this case, parts of the conductor layers that protrude from the areas of the cable core 12 and the shield wire 14 prevent the cable core 12 and the shield wire 14 from moving inwardly in the A1 direction, and at the same time, the conductor layers 52 and 54 are conductively connected to the cable core 12 and the shield wire 14, respectively, on the cable-assembly end surface S.

Figure 5:
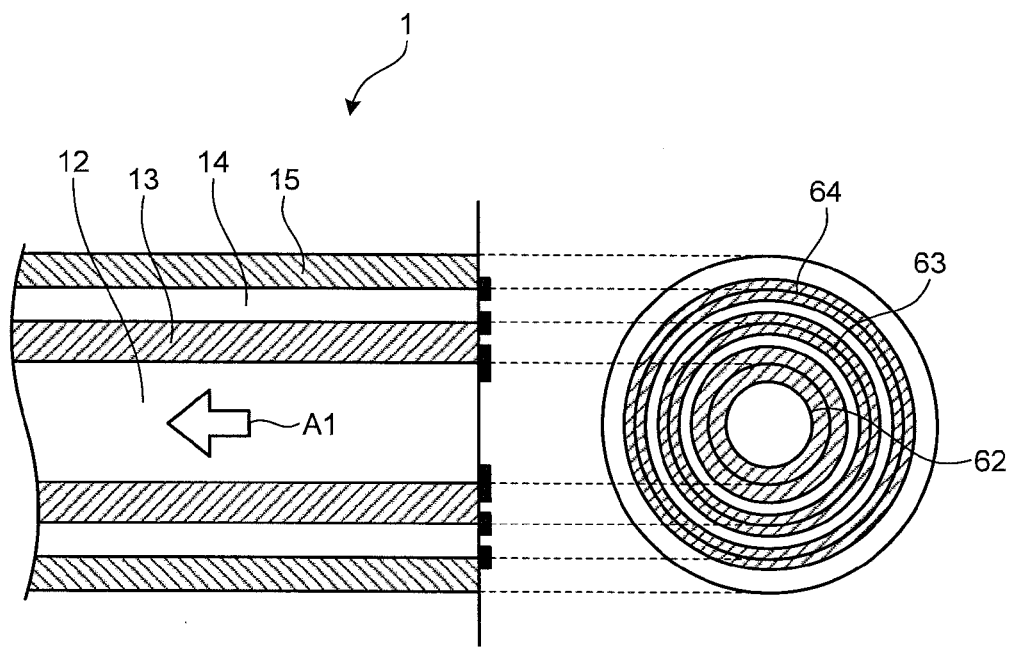
FIG. 5 is a cross-sectional view of a modification of the conductor layer.

Also, as illustrated in FIG. 5, ring-like shaped conductor layers 62, 63, 64 may be applied, which are only formed near an area at which the cable core 12 and the internal insulator 13 are in contact, near an area at which the shield wire 14 and the internal insulator 13 are in contact, and near an area at which the shield wire 14 and the external insulator 15 are in contact. Although the conductor area is reduced with this arrangement, inward movement of the cable core 12 and the shield wire 14 is prevented.

Figure 6:
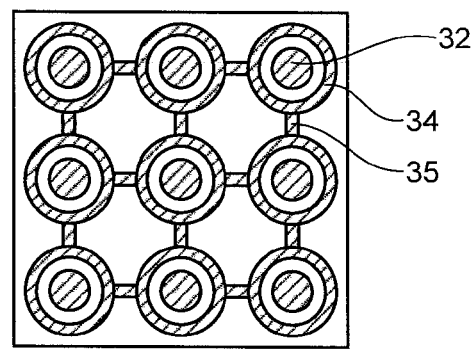
FIG. 6 is a cross-sectional view of a modification of the conductor layer that covers a shield wire.

Furthermore, as illustrated in FIG. 6, in the case in which the shield wire 14 of each of the cables 11 is a shield wire having a common potential, it is preferable to connect the conductor layers 34 to each other via a conductor layer 35. This facilitates connection of the shield wires 14 and reduces contact noises more effectively. This, especially, allows a shield area on the side of an external connecting terminal to be formed at one position.

Figure 7:
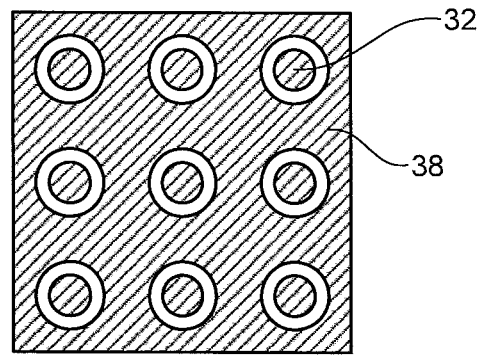
FIG. 7 is a cross-sectional view of a modification of the conductor layer that covers a shield wire.

Similarly, as illustrated in FIG. 7, the areas between the adjacent shield wires 14 may be covered with a conductor layer 38. In other words, the entire area on the cable-assembly end surface S other than the areas of the cable core 12 and the internal insulator 13 may be covered with the conductor layer 38.

Figure 8:
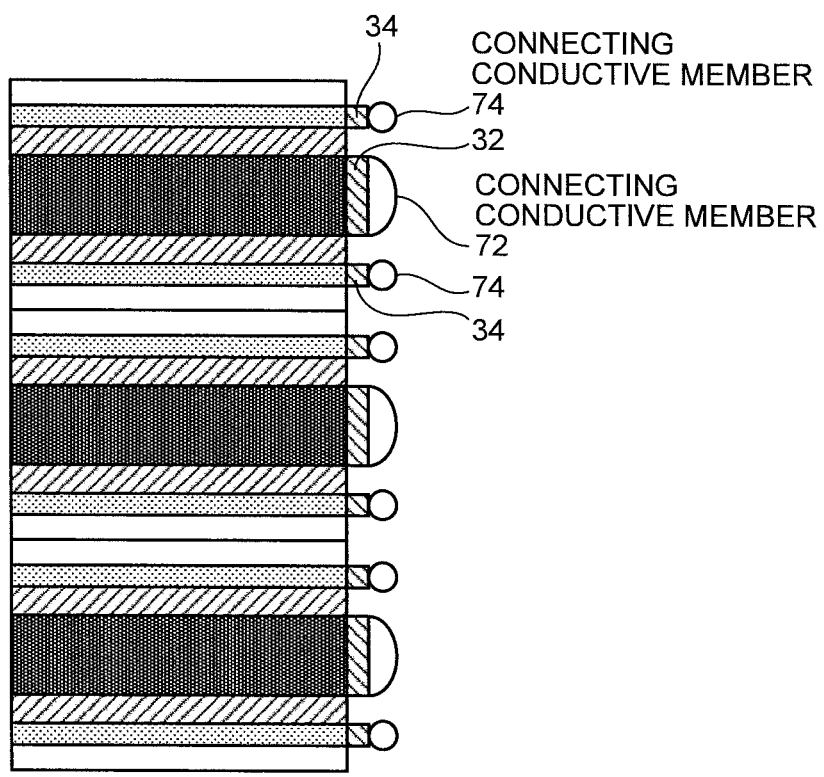
FIG. 8 is a cross-sectional view of a modification in which a connecting conductive member is provided.

Also, as illustrated in FIG. 8, connecting conductive members 72 and 74, which are solder projections, may be further formed on the conductor layers 32 and 34, respectively. The solder projections are formed by applying solder pastes or solder powders to the surfaces of the connecting ends of the cable core 12 and the shield wire 14, and then fusing the solder by reflow. Because the solder projections can be directly used as connecting members that connect the cable assembly 1 to the external substrate 40, this simplifies a connecting-material supplying process in connecting the cable assembly 1 to the substrate 40.

Figure 9:
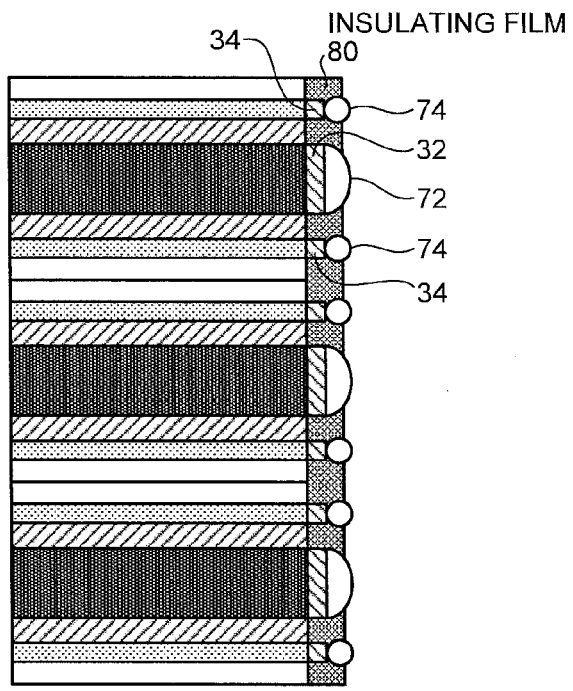
FIG. 9 is a cross-sectional view of a modification in which a connecting conductive member and an insulating film are provided.

Furthermore, as illustrated in FIG. 9, a resist may be applied between the connecting conductive members 72, 74 and the conductor films 32, 34 as an insulating film 80. In this case, the thickness of the insulating film 80 is such that the distal ends of the connecting conductive members 72 and 74 are exposed. With this, a short-circuit between the cable core 12 and the shield wire 14 can be prevented.

Figure 10:
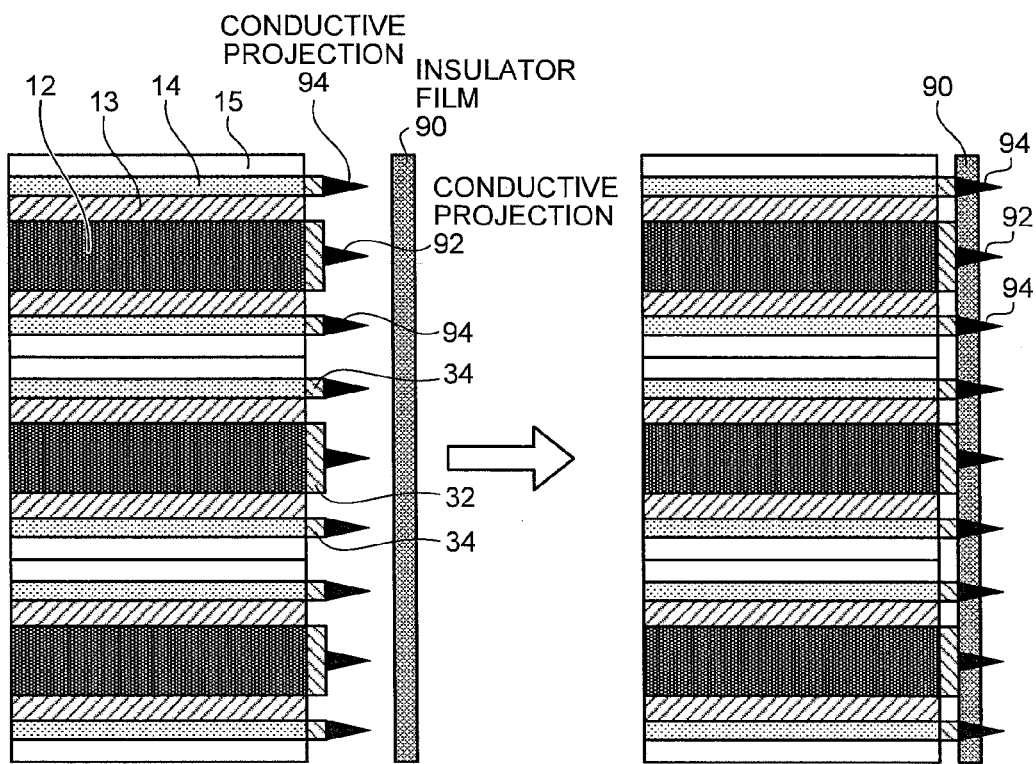
FIG. 10 is a cross-sectional view of a modification in which a conductive projection and an insulator film are provided.

Also, as illustrated in FIG. 10, conductive projections 92 and 94 may be formed on the conductor layers 32 and 34 of the connecting end surfaces of the cable core 12 and the shield wire 14, respectively, by supplying an Ag paste to form projections and then hardening the projections by a heat. Furthermore, the cable-assembly end surface S is covered with an insulator film 90 and cause the conductive projections 92 and 94 to pierce through the insulator film 90 so that the distal ends of the conductive projections 92 and 94 are exposed on the surface of the insulator film 90. With this, a short-circuit between the conductive projections 92 and 94 is prevented. Because the insulator film 90 is especially used in this case, an applying process of insulator, etc., is unnecessary; therefore, an insulating process can be performed easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable assembly comprising:
   a cable group in which a plurality of cables are bound together, each of the plurality of cables having at least a cable core and an internal insulator formed on an outer circumference of the cable core;
   a cable fixing member for binding the plurality of cables together into the cable group;
   a conductor layer provided, corresponding to at least a portion of a cross section of the cable core, on a connecting end surface, the connecting end surface being formed by cutting the cable group along a cutting plane fixed by the cable fixing member and by polishing the cutting plane that leads to the cable group.

2. The cable assembly according to claim 1, wherein the conductor layer is formed to be inserted into a gap between the cable core and the internal insulator near the connecting end surface.

3. The cable assembly according to claim 1, wherein a width of the conductor layer exceeds a width of the cable core so that a part of the conductor layer is provided on an area corresponding to the internal insulator.

4. The cable assembly according to claim 1, further comprising additional conductor layers, wherein each of the plurality of cables includes a shield wire on an outer circumference of the internal insulator and an external insulator on an outer circumference of the shield wire, wherein the conductor layer and the additional conductor layers are arranged in concentric rings on a first boundary area where the cable core and the internal insulator are in contact, on a second boundary area where the shield wire and the internal insulator are in contact, and on a third boundary area where the shield wire and the external insulator are in contact, wherein the conductor layer and the additional conductor layers are not in contact with one another.

5. The cable assembly according to claim 1, wherein the cable fixing member is a resin that at least encases an outer periphery of the cable group.

6. A cable assembly comprising:
a cable group in which a plurality of cables are bound together, each of the plurality of cables having at least a cable core and an internal insulator formed on an outer circumference of the cable core;
a cable fixing means for binding the plurality of cables together into the cable group;
a conductor means provided, corresponding to at least a portion of a cross section of the cable core, on a connecting end surface, the connecting end surface being formed by cutting the cable group along a cutting plane fixed by the cable fixing means and by polishing the cutting plane that leads to the cable group.

* * * * *